(12) United States Patent
Fowler

(10) Patent No.: US 8,721,703 B2
(45) Date of Patent: *May 13, 2014

(54) ADHESIVE COATED STENT AND INSERTION INSTRUMENT

(75) Inventor: David N. Fowler, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/446,207

(22) Filed: Apr. 13, 2012

(65) Prior Publication Data

US 2012/0197275 A1 Aug. 2, 2012

Related U.S. Application Data

(63) Continuation of application No. 11/634,540, filed on Dec. 5, 2006, now Pat. No. 8,177,798.

(51) Int. Cl.
*A61B 17/08* (2006.01)

(52) U.S. Cl.
USPC ............................ 623/1.11; 227/19; 606/153

(58) Field of Classification Search
USPC ............... 606/153, 219; 623/1.11, 23.7, 1.13;
227/179.1, 176.1, 180.1, 175.1–175.4,
227/177.1, 178.1, 181.1, 182.1, 19
See application file for complete search history.

(56) References Cited

U.S. PATENT DOCUMENTS

| | | | |
|---|---|---|---|
| 5,395,030 A | 3/1995 | Kuramoto et al. | |
| 5,779,729 A * | 7/1998 | Severini | 623/1.15 |
| 6,245,076 B1 | 6/2001 | Yan | |
| 6,602,287 B1 | 8/2003 | Millare et al. | |
| 6,635,078 B1 | 10/2003 | Zhong et al. | |
| 6,682,540 B1 | 1/2004 | Sancoff et al. | |
| 6,726,923 B2 | 4/2004 | Iyer et al. | |
| 6,776,792 B1 | 8/2004 | Yan et al. | |
| 6,838,493 B2 | 1/2005 | Williams et al. | |
| 6,867,247 B2 | 3/2005 | Williams et al. | |
| 6,958,073 B2 | 10/2005 | Rogers et al. | |
| 7,001,425 B2 | 2/2006 | McCullagh et al. | |
| 7,066,934 B2 | 6/2006 | Kirsch | |
| 7,179,883 B2 | 2/2007 | Williams et al. | |
| 7,708,180 B2 * | 5/2010 | Murray et al. | 227/175.1 |
| 8,177,798 B2 * | 5/2012 | Fowler | 606/153 |

(Continued)

FOREIGN PATENT DOCUMENTS

WO WO 2006/003486 A1 1/2006
WO WO 2006/044490 A 4/2006

OTHER PUBLICATIONS

European Search Report for EP 11004918.6-1257 date of completion is Jul. 26, 2011 (3 pages).

(Continued)

*Primary Examiner* — Tuan V Nguyen
*Assistant Examiner* — Tin Nguyen

(57) ABSTRACT

A deployment cartridge is provided to insert a coated stent into a junction formed between to tubular tissue sections. The deployment cartridge includes a pusher and a coated stent contained within the pusher. The pusher includes support structure for engagement with the stent. The stent is coated with a tissue sealant or tissue adhesive. An insertion instrument is also disclosed for advancing the deployment cartridge into the junction formed between the two tubular tissue sections. There is also disclosed a method of facilitating the support and healing at a juncture formed between tubular tissue sections with a coated stent.

9 Claims, 5 Drawing Sheets

(56) References Cited

U.S. PATENT DOCUMENTS

| | | | |
|---|---|---|---|
| 2001/0004699 A1 | 6/2001 | Gittings et al. | |
| 2001/0047179 A1* | 11/2001 | Gifford, III et al. | 606/153 |
| 2002/0042650 A1 | 4/2002 | Vardi et al. | |
| 2003/0004209 A1 | 1/2003 | Hunter et al. | |
| 2003/0105516 A1 | 6/2003 | Austin | |
| 2004/0098119 A1 | 5/2004 | Wang | |
| 2004/0210235 A1 | 10/2004 | Deshmukh et al. | |
| 2004/0210299 A1 | 10/2004 | Rogers et al. | |
| 2004/0220682 A1* | 11/2004 | Levine et al. | 623/23.65 |
| 2004/0236399 A1 | 11/2004 | Sundar | |
| 2005/0004646 A1 | 1/2005 | Moriarty, Jr. | |
| 2005/0070921 A1 | 3/2005 | Ortiz et al. | |
| 2005/0110214 A1* | 5/2005 | Shank et al. | 273/274 |
| 2005/0267498 A1 | 12/2005 | Hendricksen et al. | |
| 2005/0288763 A1 | 12/2005 | Andreas et al. | |
| 2006/0184237 A1 | 8/2006 | Weber et al. | |
| 2006/0200221 A1 | 9/2006 | Malewicz | |
| 2007/0038248 A1* | 2/2007 | Heinrch | 606/219 |

OTHER PUBLICATIONS

European Search Report for EP 11004916.0-1257 date of completion is Oct. 4, 2011 (3 pages).

European Search Report for EP 07254473.7-1257 date of completion is Aug. 4, 2008 (10 pages).

Extended European Search Report corresponding to EP 11 00 4917.8, completed Aug. 25, 2011 and mailed Sep. 1, 2011; (10 pp).

* cited by examiner

ADHESIVE COATED STENT AND INSERTION INSTRUMENT

CROSS-REFERENCE TO RELATED APPLICATIONS

This application is a continuation of U.S. patent application Ser. No. 11/634,540 filed Dec. 5, 2006 now U.S. Pat. No. 8,177,798, and the disclosure of which is hereby incorporated by reference in its entirety.

BACKGROUND

1. Technical field

The present disclosure relates to the use of an adhesive coated stent to support an anastomotic site. More particularly, the present disclosure relates to an apparatus and method for inserting an adhesive coated stent into an anastomotic site formed at a junction between tubular tissue sections.

2. Background Of Related Art

During the various surgical procedures it is often necessary to connect or join the free ends of two or more tubular tissue sections. This process is termed forming an anastomosis and the resultant junction between the tubular tissue sections is referred to as an anastomotic site. Such procedures are common in vascular surgery where it is often necessary to join vascular tissue sections during bypass operations, etc. The forming of an anastomosis is also common during colorectal surgery where a diseased portion of the colon is excised and the resultant sections are rejoined to form an anastomotic site.

The formation of an anastomosis or an anastomotic site is often achieved by folding the free ends of the tissue sections radially inwardly and securing them together. The resultant anastomotic junction typically results in a stricture which is a circumscribed narrowing of the joined hollow tissue structures. For example, in certain colorectal procedures a circular stapling apparatus is utilized to join the hollow tissue sections. The free ends of the tissue sections are everted radially inwardly and staples are passed through the everted edges. After stapling, the radially inwardly directed edges of the joined issues form a stricture which temporarily inhibit free flow of fluids or other materials through the tubular tissue sections.

Thus, it is desirable to provide a support structure for positioning within the anastomotic site to support the anastomotic site and facilitate healing of the tissue sections.

It is further desirable to provide an adhesive coating on the stent to facilitate adhesion of the stent to the tissues to promote healing of the tissues.

It is still further desirable to provide a stent having a coating of tissue sealant to assist sealing the anastomotic site and prevent leakage during healing.

SUMMARY

There is disclosed a deployment cartridge for use in inserting a stent into an anastomotic site to support the anastomotic site and facilitate the healing and joining of the tissues at the anastomotic site. The deployment cartridge generally includes a hollow pusher and a stent wholly supported within the hollow pusher. The stent is formed as a wire mesh cage having a coating formed on an outer surface. In one embodiment, the outer coating includes a tissue sealant. In an alternative embodiment, the outer coating includes a tissue adhesive. In a further embodiment, the stent includes an inner coating to facilitate the passage of materials through the stent.

The pusher includes support structure engageable with the stent to support the stent within the pusher. In one embodiment, the support structure includes at least one radially inwardly directed projection engageable with a proximal end of the stent. The pusher is formed with a sharp distal tip configured to cut tissue.

There is also disclosed an insertion instrument for use in positioning a stent within an anastomotic site. The insertion instrument generally includes a handle having an elongate member extending distally from the handle and a head extending distally from the elongate member. A deployment cartridge is disposed within the head such that the deployment cartridge may be extended out of the head. The deployment cartridge generally includes a pusher and a stent contained within the pusher. The handle includes an actuator operable to advance the deployment cartridge out of the head.

The insertion instrument additionally includes an anvil member engageable with the head. The anvil member has an abutment surface configured to engage the distal end of the stent in order to hold the stent in position within an anastomotic site as the pusher is retracted back into the head. The handle further includes an approximation knob configured to approximate the anvil relative to the head.

In one embodiment, the insertion instrument is a surgical stapling apparatus having a head including a plurality of staples and the anvil includes a plurality of anvil pockets.

There is also disclosed a method of supporting an anastomotic site with a stent. The method generally includes providing an insertion instrument having a deployment cartridge including a pusher and a stent. The insertion instrument is positioned within a first tubular tissue section and a second tubular tissue section is approximated adjacent the first tubular tissue section. The deployment cartridge is advanced into the junction formed between the first and second tubular tissue sections and the deployment cartridge is advanced into the junction.

An outer surface of the stent is provided with a coating prior to insertion of the stent within the junction formed between the first and second tissue sections. In one embodiment, the outer surface of the stent is coated with a tissue sealant while in an alternative embodiment the outer surface of the stent is coated with a tissue adhesive.

DESCRIPTION OF THE DRAWINGS

Embodiments of the presently disclosed adhesive coated stent and insertion instrument are disclosed herein with reference to the drawings, wherein.

DETAILED DESCRIPTION OF EMBODIMENTS

Embodiments of the presently disclosed adhesive coated stent and insertion instrument will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
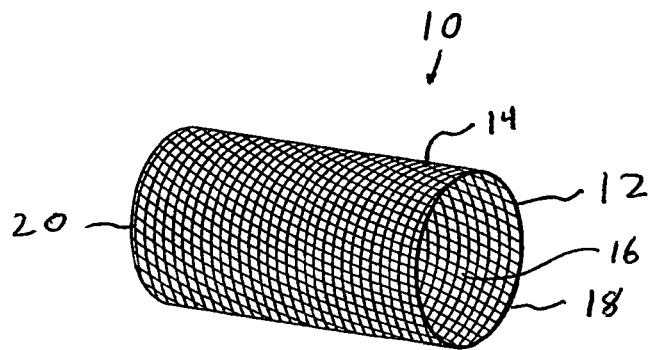
FIG. 1 is a perspective view of an adhesive coated stent.
Figure 2:
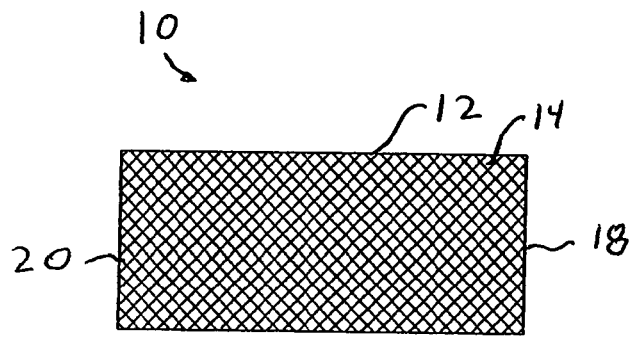
FIG. 2 is a side view of the adhesive coated stent.
Figure 3:
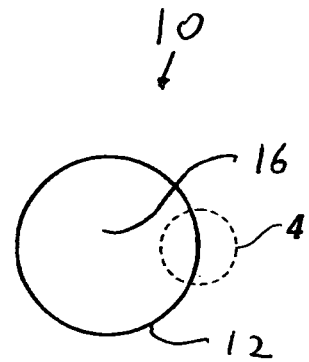
FIG. 3 is an end view of the adhesive coated stent.

FIGS. 1-3 illustrate an embodiment of the presently disclosed adhesive coated stent 10. Adhesive coated stent 10 is formed as a generally cylindrical wire mesh cage 12 having a plurality of openings or pores 14 extending through wire mesh cage 12. Wire mesh cage 12 is constructed in a manner similar to that typically used to form stents for use in vascular angioplasty surgeries. Wire mesh cage 12 may be formed from any of various suitable materials such as, for example, plastics, ceramics, or metals such as titanium, stainless steel, etc. The dimensions of pores 14 are chosen based on the intended use of wire mesh cage 12 in various surgical procedures such as, for example, vascular, colonic, etc.

Wire mesh cage 12 defines a throughbore 16 extending through cage 12 from a proximal end 18 to a distal end 20 of cage 12. Throughbore 16 provides an avenue for the flow of fluids and other matter through the tissue supported by wire mesh cage 12. It should be noted that, while wire mesh cage 12 is illustrated as a continuous cylindrical member, wire mesh cage 12 may be formed with a longitudinally split portion such that wire mesh cage 12 may be rolled inwardly upon itself to reduce its outer diameter and facilitate insertion into tissue. Once inserted into the desired tissue, wire mesh cage 12 would reexpand to its normal outer diameter after release from an insertion instrument.

Figure 4:
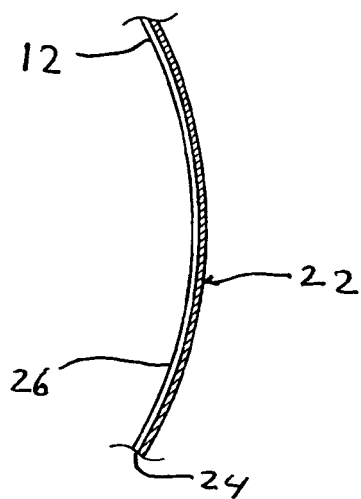
FIG. 4 is an enlarged area of detail of FIG. 3 illustrating the adhesive coating.

Referring now to FIG. 4, adhesive coated stent 10 includes an outer coating 22. Outer coating 22 consists of a tissue adhesive or sealant applied to an outer surface 24 of wire mesh cage 12. The tissue sealants may include various compositions particularly designed to allow tissue to adhere to its self including such materials as fibrin glue's, etc. Coating 22 may be applied to outer surface 24 of wire mesh cage 12 by a various known procedures, such as, for example, dipping, spraying, static or other deposition methods, etc. by incorporating coating 22 into outer surface 24 of wire mesh cage 12, adhesive coated stent 10 is particularly adapted to seal and/or adhere to the inner surfaces of tubular tissue sections in which adhesive coated stent 10 is disposed.

While not specifically shown, an inner surface 26 of wire mesh cage 12 may also be treated or coated with various materials. The materials used to coat inner surface 26 of wire mesh cage 12 would include various nonadhesive or relatively slick substances, such as, for example, Teflon, etc. to facilitate the flow of fluids and other materials through throughbore 16 of adhesive coated stent 10.

Figure 5:
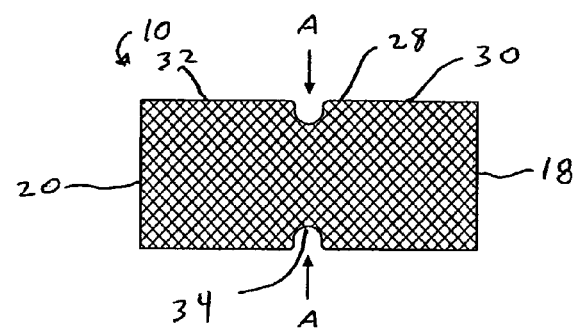
FIG. 5 is a side view of the adhesive coated stent undergoing localized compressive forces.

As best shown in FIG. 5, adhesive coated stent 10 may be formed with various areas of relatively differing strengths so as to allow adhesive coated stent 10 to conform to various areas of the tissue sections being joined. Adhesive coated stent 10 generally includes a relatively weakened central area 28 and relatively stiffened proximal and distal areas 30 and 32 extending from central area 28 towards proximal and distal ends 18 and 20 of wire mesh cage 12, respectively. As shown, when subjected to an external circumferential force A, central area 28 may deflect inwardly to form an inwardly directed circumferential recess 34. Wire mesh cage 12, and, in particular, central area 28, may be sufficiently flexible such that circumferential recess 34 slowly disappears due to the reduction in force A during healing of the joined tissue sections.

Figure 6:
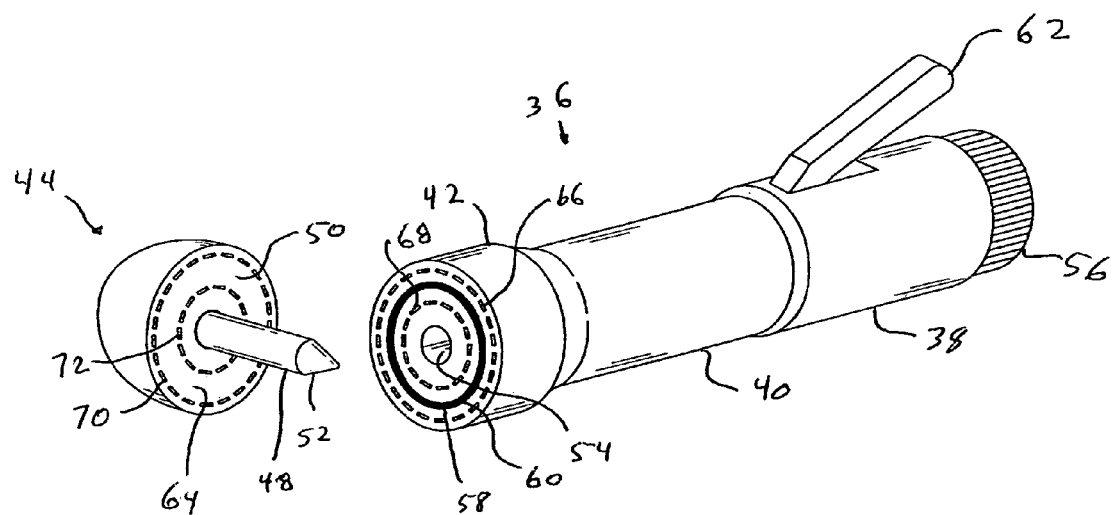
FIG. 6 is a perspective view of an insertion instrument for delivery of the adhesive coated stent.

Referring now to FIG. 6, there is disclosed an insertion instrument 36 particularly suited for insertion of adhesive coated stent 10 within an anastomotic site formed between two tubular tissue sections. Insertion instrument 36 generally includes a handle 38 having an elongate tubular member 40 extending distally from handle 38. A head portion 42 extends distally from elongate tubular member 40. Insertion instrument 36 additionally includes an anvil member 44 having a cap 46 and a shaft 48 extending proximally from cap 46. Cap 46 includes a proximal surface 50. Shaft 48 includes a proximal, tissue penetrating tip 52 for use in penetrating constricted areas of tubular tissue sections. In order to connect anvil 44 to head portion 42 of insertion instrument 36, head portion 42 includes a central bore 54 for receipt of shaft 48. Handle 38 includes an approximation knob 56 which, when actuated, serves to advance and retract shaft 48 within bore 54 so as to approximate anvil 44 relative to head portion 42 in a manner similar to that used for various commonly known surgical stapling or other fastener type apparatus. One such device, known as a EEA or end to end anastomosis instrument, is disclosed in U.S. Pat. No. 6,959,851, the entire disclosure of which is incorporated herein by reference.

Insertion instrument 36 includes a circumferential recess 58 formed in head portion 42 for receipt of a deployment cartridge 60. As discussed in more detail hereinbelow, deployment cartridge 60 includes adhesive coated stent 10 as well as a pusher member configured to advance adhesive coated stent 10 within tubular tissue sections. Handle 38 is provided with an actuator 62 to advance deployment cartridge 60 out of circumferential recess 58 formed in head portion 42. Under surface 50 of cap 48 includes an abutment surface 64 for engagement with deployment cartridge 60, and specifically with adhesive coated stent 10, to assist in retaining and separating adhesive coated stent 10 from a pusher member described in a manner hereinbelow.

Insertion instrument 36 can take the form of any of various surgical instruments typically used during surgery within tubular tissue sections. As disclosed herein, insertion instrument 36 is in the form of a surgical stapling apparatus of the type typically used to perform an end to end anastomosis procedure. In this embodiment, insertion instrument 36 includes an outer ring of staple pockets 66 and an inner ring of staple pockets 68 located radially outwardly and inwardly, respectively, of circumferential recess 58. Similarly, an outer ring of anvil pockets 70 and an inner ring of anvil pockets 72 are formed radially outwardly and inwardly, respectively, of abutment surface 64 in anvil member 44. Thus insertion instrument 36 can eject fasteners, such as, for example staples, out of staple pockets 66 and 68 and into anvil pockets 70 and 72 to thereby staple together tissue sections captured there between.

Figure 7:
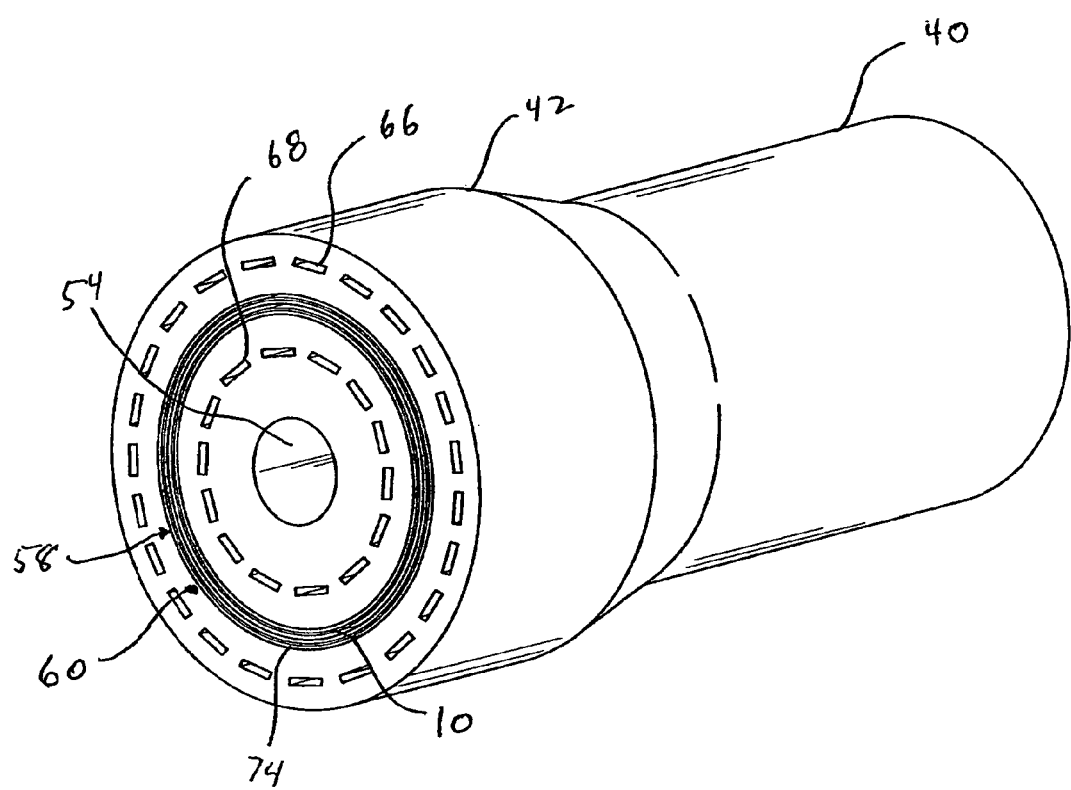
FIG. 7 is an enlarged perspective view of the distal end of the insertion instrument containing the adhesive coated stent.
Figure 8:
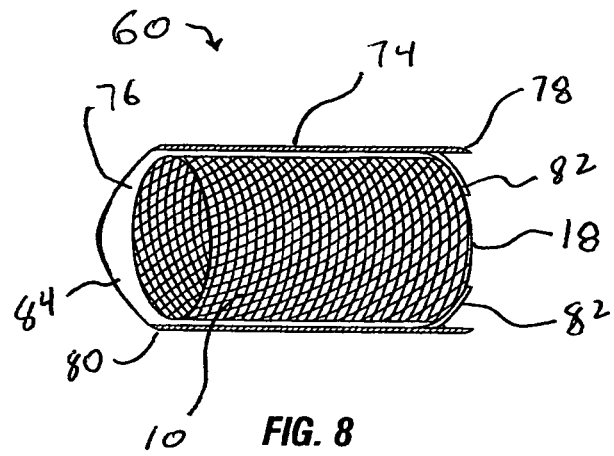
FIG. 8 is a perspective view of a pusher member of the insertion instrument containing the adhesive coated stent.

Referring now to FIGS. 7 and 8, deployment cartridge 60 will now be described. As noted hereinabove, deployment cartridge 60 includes adhesive coated stent 10 and a pusher 74 which is provided to support adhesive coated stent 10 and advance adhesive coated stent 10 out of insertion instrument 36 and into an anastomotic site formed between tubular tissue sections. Referring now specifically to FIG. 8, pusher 74 includes a throughbore 76 extending from a proximal end 78 to a distal end 80 of pusher 74. Adhesive coated stent 10 is entirely disposed within throughbore 76 of pusher 74. As shown, pusher 74 includes one or more support members 82 formed adjacent proximal end 78 and directed radially inwardly within throughbore 76 to engage and support proximal end 18 of adhesive coated stent 10. In one embodiment, pusher 74 is a circular cylindrical knife having a sharp edge or sharp tip 84 formed on distal end 80 of pusher 74. Sharp tip 84 is provided to cut through portions of tubular tissue sections after the tubular tissue sections have been stapled together.

Figure 9:
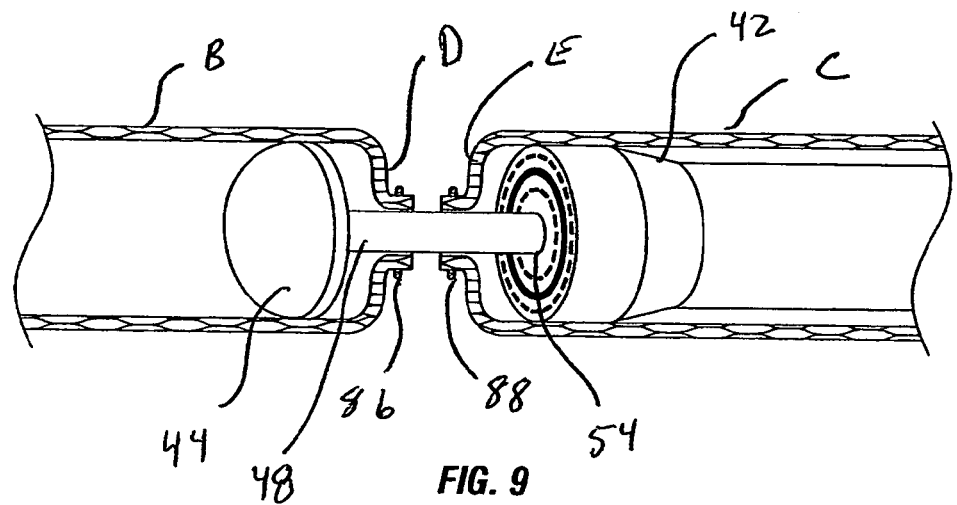
FIG. 9 is perspective view, partially shown in section, of the distal end the insertion instrument positioned in tissue.
Figure 10:
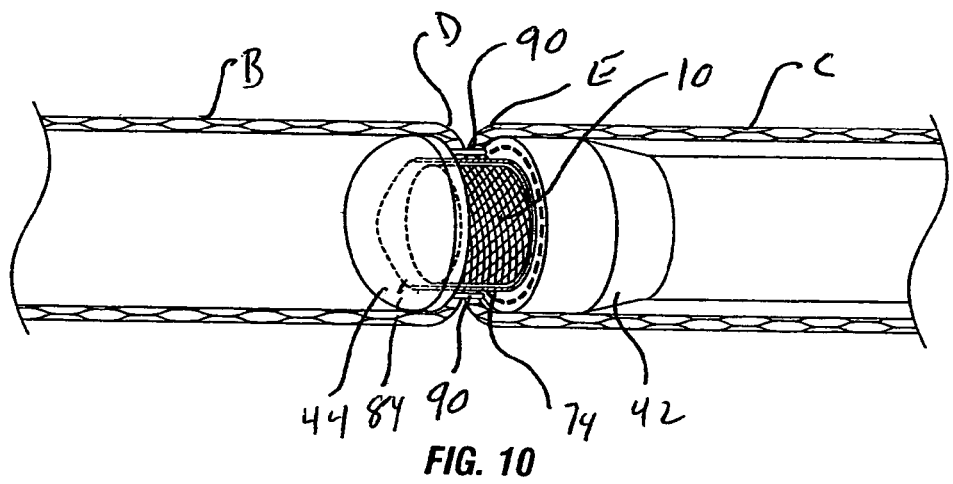
FIG. 10 is a perspective view, partially shown in section and phantom, of the insertion instrument inserting the adhesive coated stent into the tissue.
Figure 11:
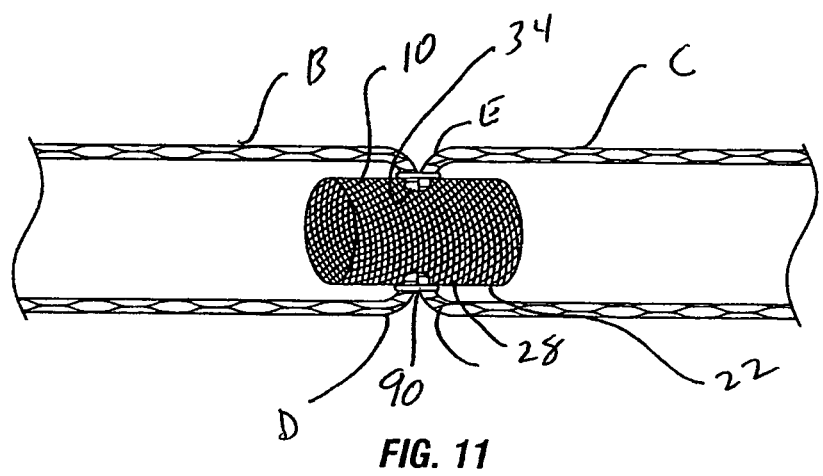
FIG. 11 is a perspective view, partially shown in section, of the adhesive coated stent supporting a stapled anastomotic site.
Figure 12:
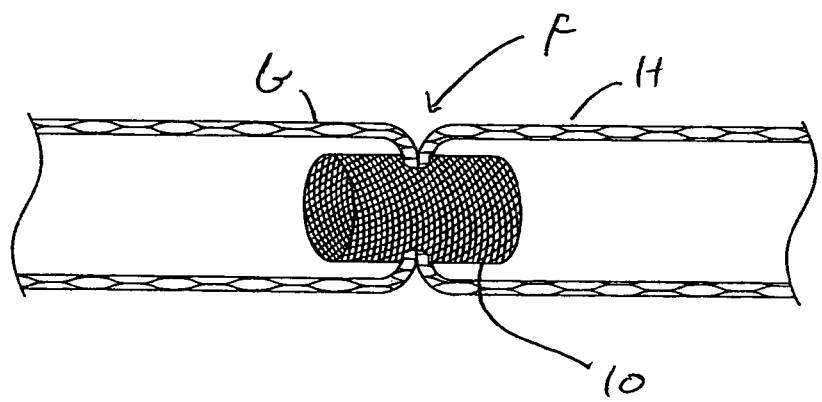
FIG. 12 is a perspective view, partially shown in section, of the adhesive coated stent supporting another anastomotic site.

The use of insertion instrument 36 to insert adhesive coated stent 10 within tubular tissue sections will now be described. Referring to FIGS. 9-11, and initially with reference to FIG. 9, in an anastomosis type surgical procedure a disease section of a tubular tissue is excised leaving a first healthy tubular tissue section B and a second healthy tubular tissue section C to be joined. First healthy tubular tissue section B has a free end D while second healthy tubular tissue section C has a free end E which are to be joined together to form an anastomosis.

Initially, anvil member 44 is positioned within the first healthy tubular tissue section B such that shaft 48 extends out of free end D. Free end D is secured to shaft 48 by sutures or ligatures 86 (which may be in the form of a "purse string") connecting free end D to shaft 48. Similarly, head 42 of insertion instrument 36 is positioned within second healthy tubular tissue section C adjacent free end E. In the initial position, deployment cartridge 60 is wholly contained within head portion 42. Once properly positioned, shaft 48 is inserted within recess 54 formed in head 42 of insertion instrument 36. Thereafter, free end E is secured about shaft 48 by sutures or ligatures 88. Thereafter, approximation knob 56 is actuated to draw anvil member 44 together against head 42 to approximate first and second healthy tissue sections B and C.

Referring now to FIG. 10, once approximated, actuator 62 of insertion instrument 36 is actuated to drive staples 90 out of respective staple pockets 66 and 68, through tissues B and C and into anvil pockets 70 and 72 thereby stapling together free ends D an E to form an anastomosis between tissue sections B and C. Continued activation of actuator 62 drives deployment cartridge 60, including pusher 74 and adhesive coated stent 10 out of head 42 and across the anastomosis formed between tissue sections B and C. as noted hereinabove, pusher 74 includes a sharp distal tip 84 which cuts through the excess tissue and allows adhesive coated stent to be advanced against abutment surface 64 of anvil member 44. Abutment surface 64 serves as a surface against which sharp distal tip 84 can engage. Abutment surface 64 additionally forms a surface to temporarily contact and engage distal end 20 (FIG. 5) of adhesive coated stent 10 such that upon withdrawal of pusher 74 back within head 42 of insertion instrument 36, adhesive coated stent 10 remains in place within tissue sections B and C.

Referring now to FIG. 11, adhesive coated stent 10 is illustrated positioned within the anastomosis formed between tissue sections B and C. As noted hereinabove, adhesive coated stent 10 includes a centrally weakened area 28 which deflects to form inwardly directed circumferential recess 34 to contain and support free ends D and E, joined by staples 90, as tissue sections B and C heal together. Once positioned, adhesive coating 22 adheres to tissue sections B and C to maintain adhesive coated stent in position. Additionally, where coating 22 includes an adhesive or sealant, the adhesive or sealant facilitates prevention of leakage through the stricture formed at the anastomotic site and allows time for the tissue sections to heal together properly.

As noted hereinabove, insertion instrument 36 may be used in situations other than stapling, to position adhesive coated stent across an anastomotic site to facilitate healing of tissues together. As shown, adhesive coated stent 10 is positioned at an anastomotic site F formed between tissue sections G and H to facilitate support and healing of the anastomotic site F.

Examples of adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively. Examples of sealants, which can be employed, include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc. Examples of hemostat materials, which can be employed, include fibrin-based, collagen-based, oxidized regenerated cellulose-based and gelatin-based topical hemostats. Examples of commercially available hemostat materials are fibrinogen-thrombin combination materials sold under the trade designations CoStasis™ by Tyco Healthcare Group, LP, and Tisseel™ sold by Baxter International, Inc. Hemostats herein include astringents, e.g., aluminum sulfate, and coagulants.

In certain preferred embodiments, the wound treatment material comprises a sealant. Such a sealant is desirably a PEG-based material. Examples of classes of materials useful as the sealant and/or adhesive include acrylate or methacrylate functional hydrogels in the presence of a biocompatible photoinitiator, alkyl-cyanoacrylates, isocyanate functional macromers with or without amine functional macromers, succinimidyl ester functional macromers with amine or sulfhydryl functional macromers, epoxy functional macromers with amine functional macromers, mixtures of proteins or polypeptides in the presence of aldehyde crosslinkers, Genipin, or water-soluble carbodiimides, anionic polysaccharides in the presence of polyvalent cations, etc.

Some specific materials which may be utilized include isocyanate terminated hydrophilic urethane prepolymers derived from organic polyisocyanates and oxyethylene-based diols or polyols, including those disclosed in U.S. Pat. Nos. 6,702,731 and 6,296,607 and U.S. Published Patent Application No. 2004/0068078; alpha-cyanoacrylate based adhesives including those disclosed in U.S. Pat. No. 6,565,840; alkyl ester based cyanoacrylate adhesives including those disclosed in U.S. Pat. No. 6,620,846; adhesives based on biocompatible cross-linked polymers formed from water soluble precursors having electrophilic and nucleophilic groups capable of reacting and cross-linking in situ, including those disclosed in U.S. Pat. No. 6,566,406; two part adhesive systems including those based upon polyalkylene oxide backbones substituted with one or more isocyanate groups in combination with bioabsorbable diamine compounds, or polyalkylene oxide backbones substituted with one or more amine groups in combination with bioabsorbable diisoycanate compounds as disclosed in U.S. Published Patent Application No. 2003/0032734, the contents of which are incorporated by reference herein; and isocyanate terminated hydrophilic urethane prepolymers derived from aromatic diisocyanates and polyols as disclosed in U.S. Published Patent Application No. 2004/0115229, the contents of which are incorporated by reference herein.

Examples of adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively. Examples of sealants, which can be employed, include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc.

In certain preferred embodiments, the wound treatment material "W" includes a sealant which is desirably a PEG-based material. Examples of classes of materials useful as the sealant and/or adhesive include acrylate or methacrylate functional hydrogels in the presence of a biocompatible photoinitiator, alkyl-cyanoacrylates, isocyanate functional macromers with or without amine functional macromers, succinimidyl ester functional macromers with amine or sulfhydryl functional macromers, epoxy functional macromers with amine functional macromers, mixtures of proteins or polypeptides in the presence of aldehyde crosslinkers, Genipin, or water-soluble carbodiimides, anionic polysaccharides in the presence of polyvalent cations, etc. Examples of sealants, which can be employed, include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc.

Surgical biocompatible wound treatment materials "W" which may be used in accordance with the present disclosure include adhesives whose function is to attach or hold organs, tissues or structures. Examples of adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively.

Some specific materials which may be utilized as adhesives include isocyanate terminated hydrophilic urethane prepolymers derived from organic polyisocyanates and oxyethylene-based diols or polyols, including those disclosed in U.S. Pat. Nos. 6,702,731 and 6,296,607 and U.S. Published Patent Application No. 2004/0068078; alpha-cyanoacrylate based adhesives including those disclosed in U.S. Pat. No. 6,565,840; alkyl ester based cyanoacrylate adhesives including those disclosed in U.S. Pat. No. 6,620,846; adhesives based on biocompatible crosslinked polymers formed from water soluble precursors having electrophilic and nucleophilic groups capable of reacting and crosslinking in situ, including those disclosed in U.S. Pat. No. 6,566,406; two part adhesive systems including those based upon polyalkylene oxide backbones substituted with one or more isocyanate groups in combination with bioabsorbable diamine compounds, or polyalkylene oxide backbones substituted with one or more amine groups in combination with bioabsorbable diisoycanate compounds as disclosed in U.S. Published Patent Application No. 2003/0032734, the contents of which are incorporated by reference herein; and isocyanate terminated hydrophilic urethane prepolymers derived from aromatic diisocyanates and polyols as disclosed in U.S. Published Patent Application No. 2004/0115229, the contents of which are incorporated by reference herein. It is contemplated that any known suitable adhesive may be used.

The stent can be an absorbable or resorbable polymer, stainless steel, titanium, or other bio-compatible material.

It will be understood that various modifications may be made to the embodiments disclosed herein. For example, various other support structure may be provided on the pusher to engage, support, and advance the adhesive coated stent out of the insertion instrument. Further, as noted hereinabove, the disclosed deployment cartridge, including the pusher and adhesive coated stent, may be utilized in insertion instruments other than stapling instruments. Therefore, the above description should not be construed as limiting, but merely as exemplifications of particular embodiments. Those skilled in the art will envision other modifications within the scope and spirit of the claims appended hereto.

The invention claimed is:

1. A surgical instrument for use at an anastomotic site comprising:
    an annular surgical stapling device having a head portion with a plurality of surgical staples disposed in first staple pockets formed within the head portion and arranged in an annular configuration and second staple pockets arranged in an annular configuration, the head portion including a circumferential recess formed therein, wherein the first staple pockets are disposed radially inward of the circumferential recess and the second staple pockets are disposed radially outward of the circumferential recess; and
    a deployment cartridge disposed within the circumferential recess of the head portion, the deployment cartridge including a tubular, wire mesh cage stent supported therein and a pusher operable to advance the stent out of the circumferential recess of the head portion of the annular surgical stapling device.

2. The surgical instrument as recited in claim 1, wherein the stent includes an outer coating.

3. The surgical instrument as recited in claim 2, wherein the outer coating includes a tissue sealant.

4. The surgical instrument as recited in claim 2, wherein the outer coating includes a tissue adhesive.

5. The surgical instrument as recited in claim 1, wherein the stent includes an inner coating to facilitate the passage of materials therethrough.

6. The surgical instrument as recited in claim 1, wherein the pusher includes support structure engageable with the stent.

7. The surgical instrument as recited in claim 6, wherein the support structure includes at least one radially inwardly directed projection for support of the stent.

8. The surgical instrument as recited in claim 1, wherein the pusher includes a sharp distal tip.

9. The surgical instrument as recited in claim 1, wherein the stent is entirely disposed within a throughbore of the deployment cartridge.

* * * * *